United States Patent [19]

Shackelford, Sr. et al.

[11] Patent Number: 5,531,754
[45] Date of Patent: Jul. 2, 1996

[54] RETRACTABLE SURGICAL BLADE DEVICE AND ASSOCIATED METHOD

[76] Inventors: Howard L. Shackelford, Sr.; Howard L. Shackelford, Jr., both of R.D. 2, 292 Dement St., Triadelphia, W. Va. 26059

[21] Appl. No.: 273,275

[22] Filed: Jul. 11, 1994

Related U.S. Application Data

[63] Continuation of Ser. No. 131,047, Oct. 1, 1993, abandoned, which is a continuation-in-part of Ser. No. 867,609, Jul. 24, 1992, abandoned.

[51] Int. Cl.[6] .............................. A61B 17/32; B26B 3/06
[52] U.S. Cl. .................. 606/167; 30/162; 30/335
[58] Field of Search ...................... 606/166, 167, 606/170, 172; 30/51, 162, 335

[56] References Cited

U.S. PATENT DOCUMENTS

| | | | |
|---|---|---|---|
| D. 264,799 | 6/1982 | Osada. | |
| D. 264,800 | 6/1982 | Osada. | |
| D. 264,801 | 6/1982 | Osada. | |
| D. 264,803 | 6/1982 | Machida. | |
| 2,285,155 | 6/1942 | Frost | 30/162 |
| 2,413,082 | 12/1946 | Skaer | 30/151 |
| 3,171,201 | 3/1965 | Carifi | 30/162 |
| 4,089,112 | 5/1978 | Richards | 30/335 |
| 4,103,421 | 8/1978 | Quenot | 30/335 |
| 4,499,898 | 2/1985 | Knepshield et al. | 606/167 |
| 4,615,118 | 10/1986 | Ihata. | |
| 4,729,168 | 3/1988 | Yeh. | |
| 4,735,202 | 4/1988 | Williams | 606/167 |
| 5,071,426 | 12/1991 | Dolgin et al. | 606/167 |
| 5,099,578 | 3/1992 | Jan | 30/162 |
| 5,201,748 | 4/1993 | Newman et al. | 30/335 |
| 5,207,696 | 5/1993 | Matwijcow | 606/167 |
| 5,250,063 | 10/1993 | Abidin et al. | 606/167 |
| 5,258,001 | 11/1993 | Corman | 606/167 |

FOREIGN PATENT DOCUMENTS

| | | | |
|---|---|---|---|
| 2617148 | 10/1977 | Germany. | |
| 2648423 | 4/1978 | Germany. | |
| 3722899 | 1/1989 | Germany | 606/167 |
| 2113550 | 8/1983 | United Kingdom | 606/166 |

*Primary Examiner*—Gary Jackson
*Assistant Examiner*—Nancy Mulcare
*Attorney, Agent, or Firm*—David V. Radack; Eckert Seamans Cherin & Mellott

[57] ABSTRACT

A retractable surgical blade includes a handle defining a channel and a surgical blade member. The surgical blade member includes a body to which is secured a surgical blade. The body has a portion which engages the channel so that the surgical blade member can move from a cutting position in which the surgical blade projects from the handle and can be employed in a surgical procedure to a retracted position in which the surgical blade is disposed in the channel. When in the retracted position, the surgical blade is unable to cut or stab persons associated with the surgical procedure. The device further includes cooperating locking members on the handle and the body to position the surgical blade member in the desired position. An associated method of performing a surgical procedure is also disclosed.

15 Claims, 3 Drawing Sheets

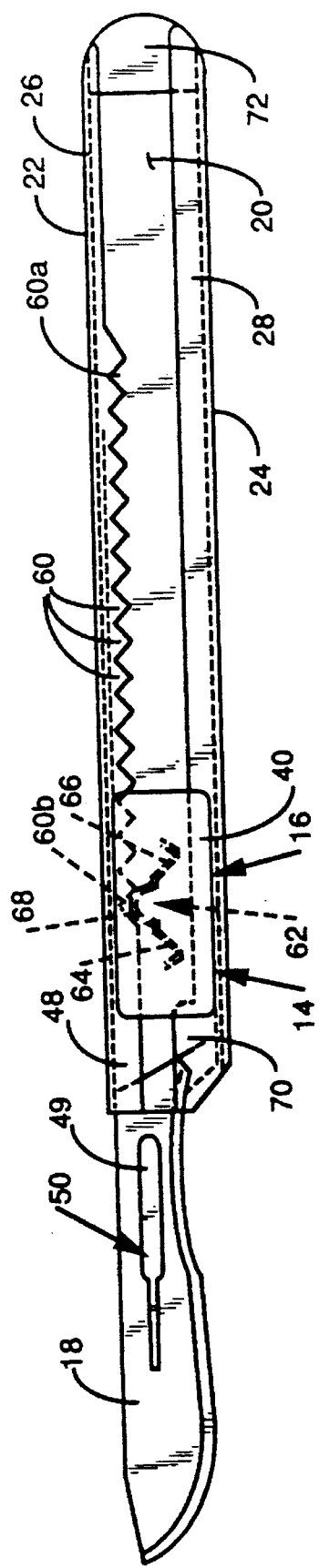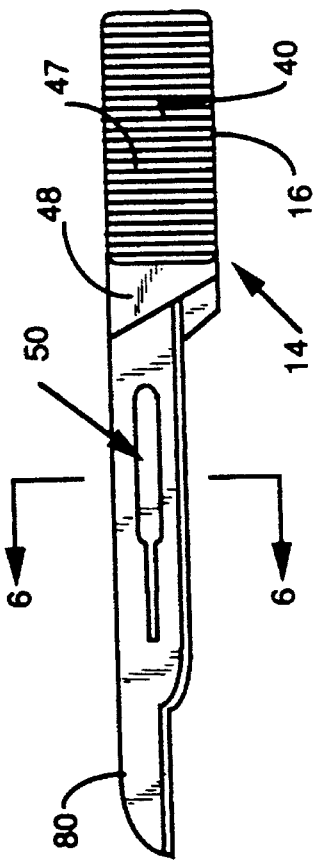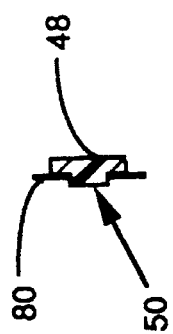

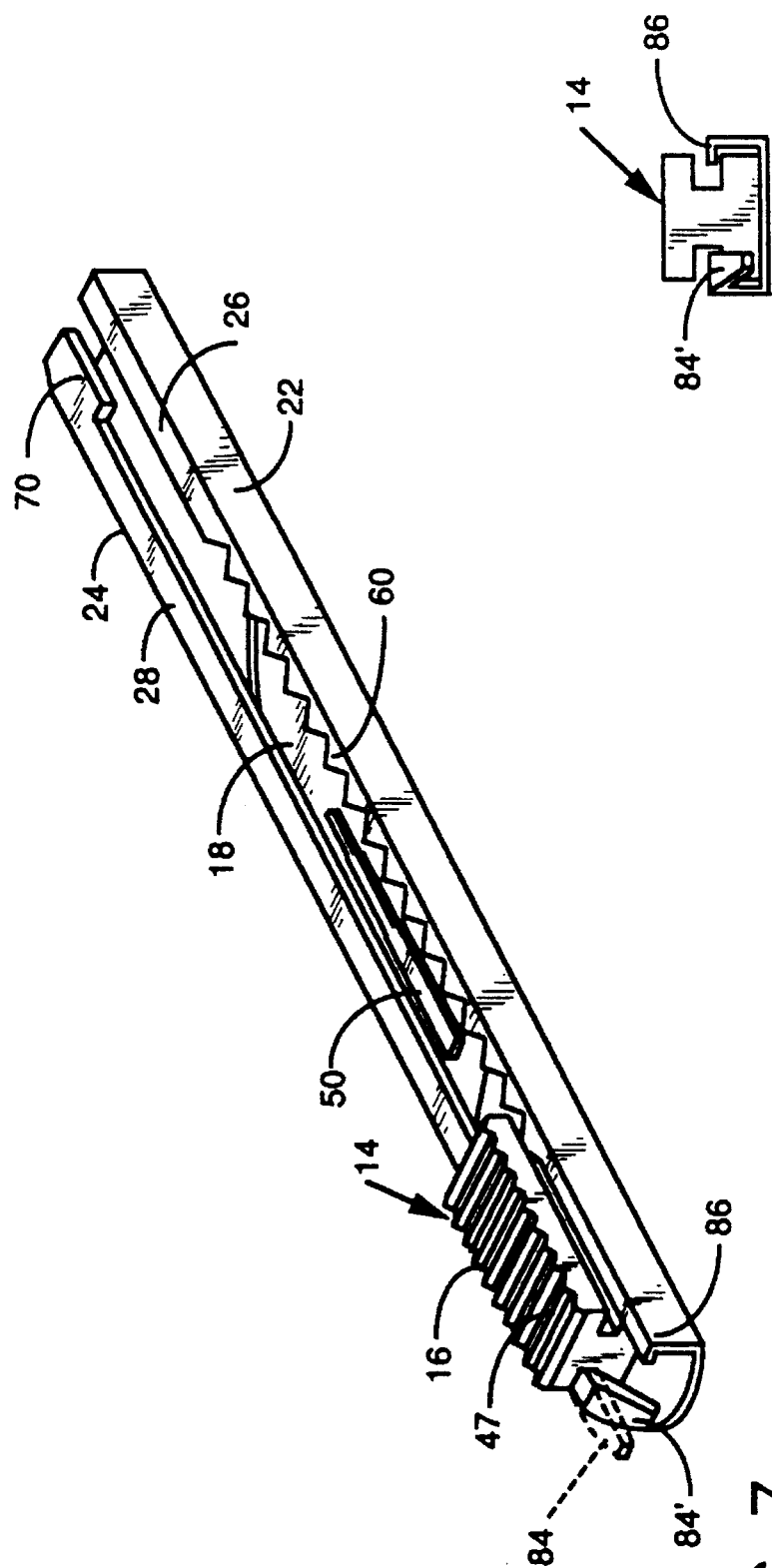

RETRACTABLE SURGICAL BLADE DEVICE AND ASSOCIATED METHOD

CROSS REFERENCE TO RELATED APPLICATIONS

This application is a file wrapper continuation of U.S. patent application Ser. No. 08/131,047, filed Oct. 1, 1993 now abandoned continuation-in-part of U.S. patent application Ser. No. 07/867,609 filed Jul. 24, 1992 in the name of Howard L. Shackelford and entitled SAFETY RETRACTABLE SCALPEL.

BACKGROUND OF THE INVENTION

This invention relates to a retractable surgical blade device and an associated method.

Surgical scalpels are well known devices used by surgeons and other medical personnel to make incisions into patients. These scalpels consist of a handle member, typically made of steel, and a removable surgical blade disposed on one end of the handle. The surgical blades, in order to be effective, are extremely sharp and must be handled carefully by all personnel involved in the surgical procedure in which the scalpel is used.

Because the scalpels have exposed blades, the chance of accidental stabbing or cutting of medical personnel is extremely great. In addition to the injury caused by the cut or stab itself, infectious viruses and/or bacteria can enter into the cut or wound during the surgical procedure. For example, AIDS can be transmitted from the blood of a surgical patient to an open wound of medical personnel inadvertently cut by the surgical blade of a scalpel.

Other than using standard surgical procedures and proceeding with caution, until now there was no way to protect medical personnel from stabbing and cutting by scalpels during surgical procedures. Clearly, there is a need for an improved surgical blade device that resists inadvertent stabbing or cutting of medical personnel during surgical procedures.

SUMMARY OF THE INVENTION

The retractable surgical blade device and associated method have met the above need. The device comprises a handle defining a channel and a surgical blade member having a body member to which is secured a surgical blade. The body member has a portion which engages the channel so that the surgical blade member can move between (a) a cutting position in which the surgical blade projects from the handle to permit the device to be employed in a surgical procedure and (b) a retracted position in which the surgical blade is disposed in the channel. When in the retracted position, the surgical blade is unable to cut or stab persons associated with the surgical procedure. The device further includes cooperating locking members on the handle and the body member to position and secure the device in the desired position.

The method of the invention involves providing a retractable surgical blade device as described above in the retracted position and moving the surgical blade member into the cutting position. A surgical procedure is then performed. The surgical blade member is then moved from the cutting position back into the retracted position.

It is an object of the invention to provide a surgical blade device which greatly reduces the incidence of inadvertent stabbing and cutting of medical personnel during surgical procedures.

It is a further object of the invention to provide a surgical blade device that is easy to use.

It is still a further object of the invention to provide a surgical blade device that can be safely disposed of after the surgical procedure is completed.

It is yet another object of the invention to provide a surgical blade device that has a surgical blade body member that can be placed in numerous positions in the handle of the device.

It is still another object of the invention to provide a surgical blade device that is adapted to be used with different sizes and types of surgical blades.

It is still yet another object of the invention to provide a method of performing a surgical procedure using a retractable surgical blade device.

These and other objects of the invention will be more fully understood from the following description of the invention with reference to the drawings appended hereto.

BRIEF DESCRIPTION OF THE DRAWINGS

FIG. 4 is a top plan view showing the device in the cutting position.

FIG. 5 is a top plan view of the surgical blade member showing a different surgical blade.

FIG. 6 is a cross-sectional view taken along line 6—6 of FIG. 5.

FIG. 7 is a perspective view showing an embodiment of the stop means of the invention which comprises a cantilevered section of the flange of the handle before the cantilevered section is crimped to form stop means.

FIG. 8 is an end view of the embodiment of FIG. 7 only showing the cantilevered section in its crimped position.

DETAILED DESCRIPTION

Figure 1:
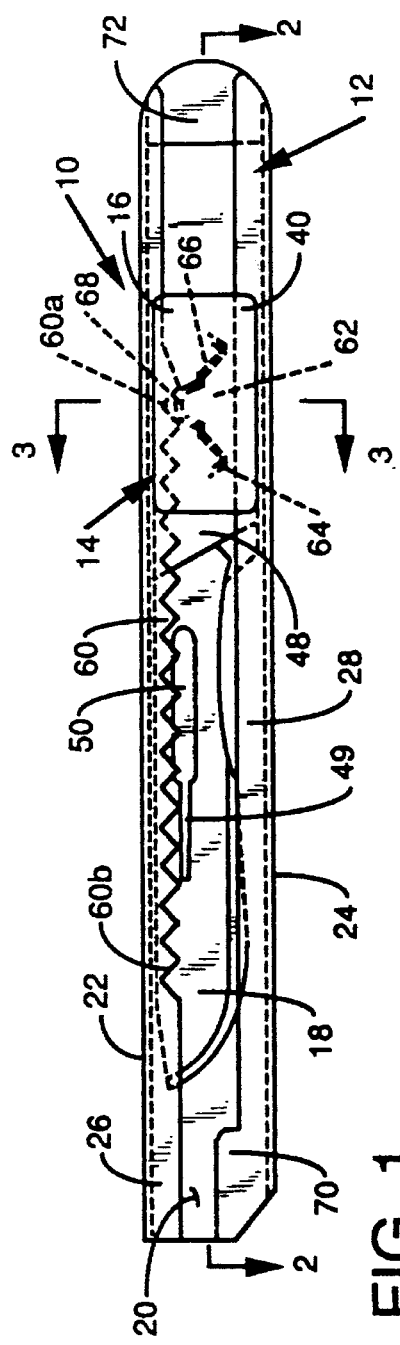
FIG. 1 is a top plan view of an embodiment of a retractable surgical blade device made in accordance with the invention.
Figure 2:
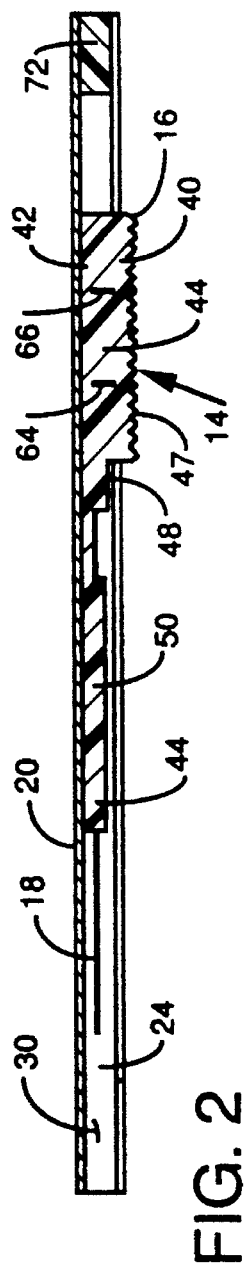
FIG. 2 is a cross-sectional view taken along line 2—2 of FIG. 1.
Figure 3:
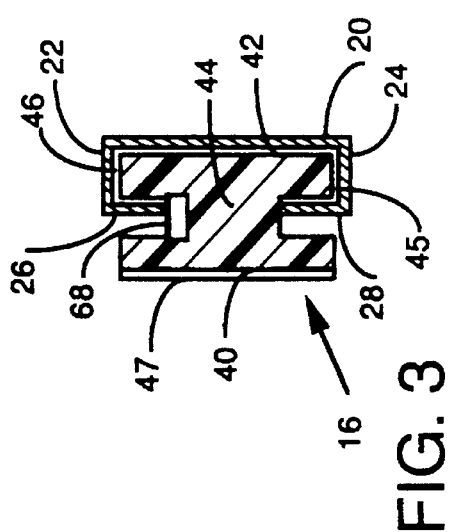
FIG. 3 is a cross-sectional view taken along line 3—3 of FIG. 1.

Referring now to FIGS. 1–3, a retractable surgical blade device 10 made in accordance with the invention is shown. The device 10 consists of a handle member 12 and surgical blade member 14 which is adapted for slidable movement in the handle member 12. The surgical blade member 14 further consists of a body member 16 to which is secured a unitary surgical blade 18.

The handle member 12 consists of a base wall 20, two elongated generally parallel longitudinal sidewalls 22 and 24 which extend generally perpendicularly from the longitudinal edges of the base wall 20 and two elongated longitudinal flanges 26 and 28 which extend generally perpendicularly from the longitudinal edges of the respective sidewalls 22 and 24. The handle member 12, therefore, defines a channel 30 (FIG. 3) in which the surgical blade member 14 is slidably movable. It will be appreciated that the handle member 12 can be made of any suitable material, such as steel or plastic, and can be either for a one-time use (disposable) or for multiple uses.

As can best be seen in FIG. 3, the body member 16 has a cross-sectional shape of an "I-beam" consisting of a top portion 40, a bottom portion 42 and an interconnecting intermediate portion 44. The body member 16 shape defines a pair of opposed longitudinal slots 45, 46. Flanges 26 and 28 engage into slots 45, 46 respectively and cooperate to guide and maintain the surgical blade member 14 in the channel 30. The bottom portion 42 is disposed in the channel 30, while top portion 40 includes an engaging section which extends above the handle member 12 to facilitate grasping and moving the surgical blade member 14 in the channel 30. The engaging section has an engaging surface 47 which is preferably serrated in order to further enhance the users grip on the body member 16 of the surgical blade member 14. It will be appreciated that the body member 16 can be made of any suitable material such as steel or plastic and can also be designed for one-time (disposable) use or multiple uses.

The surgical blade 18 is secured to a flange portion 48 of the body member 16 as can best be seen in FIGS. 1 and 2. The surgical blade 18 defines an aperture 49 which is snap-fit onto a projection 50 disposed on flange portion 48. The surgical blade 18, therefore, can be easily removed and replaced by another surgical blade. This aspect of the invention will be discussed further below with respect to FIGS. 5 and 6.

The surgical blade member 14 is shown in FIG. 1 in its "retracted position". In this position, the surgical blade member 14 is retracted entirely into channel 30 thus the surgical blade 18 is not exposed. While in the retracted position, the device 10 can be handled by medical personnel and others and can be stored without the danger of the surgical blade 18 causing a stab or other type of wound. In addition, once the device 10 is disposed of when in the retracted position, waste processing personnel are also protected against inadvertent stab or cut wounds.

The surgical blade member 14 is held in the retracted position by cooperating locking members on the handle member 12 and the body member 16 of surgical blade member 14. The locking members consist of a plurality of notches 60 formed into flange 26 and resilient spring clip member 62, shown in phantom line drawing in FIG. 1, which engages into the notches 60 to prevent sliding movement of the surgical blade member 14 when it is placed in the desired position. The spring clip member 62 has two end portions 64 and 66 which are embedded in the body member 16 (FIGS. 1 and 2) and a projecting portion 68 which projects from the interconnecting intermediate portion 44 of the body member 16 as can best be seen in FIG. 3. The projecting portion 68 engages into notch 60a to hold the surgical blade member 14 in the retracted position as is shown in FIG. 1.

It will be appreciated that the surgical blade member 14 can be placed into discrete positions between the cutting position and the retracted position by disposing the projection 68 in the intermediate notches 60 between notches 60a and 60b.

In operation, when it is desired to use the device 10 in a surgical procedure, the engaging surface 47 is grasped preferably by a user's thumb and the surgical blade member 14 is extended to a "cutting position" shown in FIG. 4. In the cutting position, the surgical blade 18 is exposed and ready for use in a surgical procedure. It will be appreciated that the surgical blade member 14 slidably moves from the retracted position shown in FIG. 1 to the cutting position shown in FIG. 4 by the user applying a force on the surgical blade member 14 to translate the surgical blade member 14 in the channel 30. The spring clip member 62, because of its resilience, slides over the intermediate notches until it reaches notch 60b. Notch 60b and the projecting portion 68 of the spring clip member 62 position and lock the surgical blade member 16 in the cutting position.

As used herein, the term "surgical procedure" means a procedure involving an incision performed by medical personnel, including doctors, nurses, emergency medical technicians and other paraprofessionals, on a human or animal patient wanting or needing medical assistance in a hospital, doctor's office, or other location where medical attention is needed or desired, such as an accident scene.

The device 10 also has stop means located at both ends thereof. One of the stop means consists of an extension section 70 of flange 28. As can be seen in FIG. 4, when the surgical blade member 14 is in the cutting position, the body member 16 abuts extension section 70 to prevent further leftward movement (FIG. 4) of the surgical blade member 14. This prevents the surgical blade member 14 from disengaging from the handle member 12 at the left end of the handle member 12. Another stop means is provided on the other end of the handle member 12. This stop means consists of a plug 72 which fits into the channel 30 at the right most end of the handle member 12. This prevents the surgical blade member 14 from disengaging from the handle member 12 at the right end of the handle member 12.

When the surgical procedure is completed, the user merely slides the surgical blade member 14 back into the retracted position. At this point, if desired, the entire device 10 can be disposed of or the surgical blade member 14 can be removed after removing plug 72.

FIGS. 5 and 6 shows another embodiment of a surgical blade member in which like parts of surgical blade member 16 are labelled with like reference characters. The surgical blade member 16 of FIG. 5 has a different type of surgical blade 80 than was shown in FIGS. 1–4. As can be seen in FIG. 6, the blade 80 is snap fit onto the projection 50 in the flange portion 48 of body member 16 of the surgical blade member 14. It will be appreciated that the invention contemplates utilizing any type of surgical blade. Surgical blades are conventionally labelled with a number such as "10", "11", "15" etc and have a standard sized aperture 49 which engages projection 50. The invention contemplates use with these standard sized blades but can also be modified to accommodate other sizes and types of surgical blades.

As was mentioned above, the entire device 10 can be made for a one-time use in which the device 10 is used for a surgical procedure and, after being placed in the retracted position, is then disposed of properly. In this case, the device 10 can be packaged in a sterile sealed package 10', as shown in FIG. 7, which is opened when it is desired to use the device 10. It will be appreciated that instead of properly disposing the entire device 10, as is preferred, the surgical blade member 14 only can be removed from the handle member 12 and disposed of properly. Finally, only the surgical blade 18 need be removed from the surgical blade member 14 and replaced with another surgical blade 80, after which the surgical blade member 14 containing the new surgical blade 80 can be placed back into the handle member 12. The replaced surgical blade 18 should then be disposed of properly.

FIG. 7 shows another embodiment of the stop means of the invention. Instead of plug 72, flange 26 has a cantilevered end portion 84 shown in phantom in FIG. 7 that can be crimped to form a crimped section 84' as shown in solid line on FIG. 7 and as can been seen also in FIG. 8. In this way, the crimped section 84' prevents the surgical blade member 14 from becoming accidentally disengaged from the handle member 12 of the right end of the handle member 12, similarly to plug 72. It is preferred that crimped section 84' be used with the disposable embodiment of the device 10 as it will be appreciated that it is more difficult to remove the surgical blade member 14 from the handle member 12 in order to replace the surgical blade 18 and reuse the surgical blade member 14. However, if desired, crimped section 84' can be straightened such as by using pliers or other hand tools so that the surgical blade member 14 can be removed from the handle member 12.

The method of the invention involves providing the retractable surgical blade device 10 as described above in the retracted position and then moving the surgical blade member 14 into a cutting position in which the surgical blade 18 projects from the handle 12. Once in the cutting position, an incision is made into the patient and a surgical procedure is performed. After performing the surgical procedure, the surgical blade member 14 is moved into the retracted position so that the surgical blade is unable to cut or stab persons associated with a surgical procedure.

The device 10 shown in FIGS. 1–8 is preferably grasped by a user's right hand so that the user's thumb can engage the engaging surface 47 to move the surgical blade member 14 in the channel 30. The invention contemplates also a "left hander's" version of the device, which is essentially a mirror image of device 10, such that the device can be grasped and used efficiently with a user's left hand.

It will be appreciated that a retractable surgical blade device and an associated method of performing a surgical procedure are provided which greatly reduces the incidence of inadvertent stab or cut wounds to medical personnel and others involved in handling the device.

Whereas particular embodiments of the invention have been described above for purposes of illustration, it will be evident to those skilled in the art that numerous variations of the details may be made without departing from the invention as defined in the appended claims.

What is claimed is:

1. A retractable surgical blade device comprising:

a handle having a front end and a back end, said handle including a base wall and a pair of opposed sidewalls extending generally perpendicularly from said base wall, said sidewalls each including a flange extending generally perpendicularly therefrom;

said base wall, said sidewalls and said flanges defining a channel;

a surgical blade member having a body member which defines a pair of opposed longitudinal slots and a surgical blade secured to said body member;

said flanges engaging into said slots to guide and maintain said surgical blade member in said channel;

said surgical blade member being movable between a cutting position wherein said surgical blade projects from said front end of said handle and said device can be employed in a surgical procedure and a retracted position wherein said surgical blade is disposed in said channel so that said surgical blade is unable to cut or stab persons associated with a surgical procedure;

said handle includes a front end stop means comprising a section extending from said flange to resist said surgical blade member from disengaging from said front end of said handle and a back end stop means comprising a cantilevered end portion that is crimped to resist said surgical blade member from disengaging from said back end of said handle; and said device further including cooperating locking members on said handle and said body member, said locking members positioning and securing said surgical blade in a desired position.

2. The device of claim 1, wherein said surgical blade member is slidably movable in said channel between said retracted position and said cutting position.

3. The device of claim 1, wherein said cooperating locking members include at least two notches in one of said flanges and means on said body member adapted to engage into said notches, wherein said projection engages into a first said notch when said surgical blade member is in said cutting position and said projection engages into a second said notch when said surgical blade member is in said retracted position.

4. The device of claim 3, wherein said means on said body to engage into said notches is a resilient spring clip having two ends and an intermediate portion disposed between said two ends; and each of said ends is secured to a respective portion of said body member and said intermediate portion projects from said body member to engage into said notches.

5. The device of claim 4, wherein said handle includes a plurality of notches in addition to said first and second notches for positioning said surgical blade in positions between said cutting position and said retracted position.

6. The device of claim 1, wherein said body member includes an engaging section, said engaging section being employed to move said surgical blade member in said channel.

7. The device of claim 6, wherein said engaging section includes an engaging surface having serrations in order to facilitate gripping thereof.

8. The device of claim 1, wherein said handle is made of materials selected from the group consisting of metal and plastic.

9. The device of claim 1, wherein said body member is made of materials selected from the group consisting of metal and plastic.

10. The device of claim 1, wherein said surgical blade member includes blade securement means for securing said surgical blade to said body member; and said blade securement means is a raised section on said body member and an aperture defined by said surgical blade, said raised section engaging into said aperture to snap-fit said surgical blade onto said body member.

11. The device of claim 1, wherein said handle includes two generally parallel elongated sidewalls.

12. A method of performing a surgical procedure comprising:

providing a retractable surgical blade device comprising (i) a handle having a front end and a back end, said handle including a base wall and a pair of opposed sidewalls extending generally perpendicularly from said base wall, said sidewalls each including a flange extending generally perpendicularly therefrom wherein said base wall, said sidewalls and said flanges define a channel; (ii) a surgical blade member having a body member which defines a pair of opposed longitudinal slots and a surgical blade secured to said body member, said flanges engaging into said slots to guide and maintain said surgical blade member in said channel; and (iii) said handle includes a front end stop means comprising a section extending from said flange to resist said surgical blade member from disengaging from said front end of said handle and a back end stop means comprising a cantilevered end portion that is crimped to resist said surgical blade member from disengaging from said back end of said handle;

providing said device being in a retracted position wherein said surgical blade is disposed in said channel;

moving said surgical blade member into a cutting position wherein said surgical blade projects from said front end of said handle;

performing a surgical procedure using said device while said surgical blade member is in said cutting position; and moving said surgical blade member back into said retracted position wherein said surgical blade is retracted into said channel such that said surgical blade is unable to cut or stab persons associated with a surgical procedure.

13. The method of claim 12, including after retracting said surgical blade member into said retracted position, disposing of said device.

14. The method of claim 12, including after performing said surgical procedure, replacing said surgical blade with another surgical blade; and disposing of said replaced surgical blade.

15. The method of claim 12, including storing said device in said retracted position.

* * * * *